United States Patent [19]

Stach

[11] 4,046,884
[45] Sept. 6, 1977

[54] N-(α-AMINOALKYLIDENE)PHOSPHOR- AND PHOSPHONAMIDATES, AND METHOD FOR CONTROLLING INSECTS

[75] Inventor: Leonard J. Stach, Riverside, Ill.

[73] Assignee: Velsicol Chemical Corporation, Chicago, Ill.

[21] Appl. No.: 662,667

[22] Filed: Mar. 1, 1976

[51] Int. Cl.$^2$ ............... A01N 9/36; C07F 9/24
[52] U.S. Cl. .................. 424/210; 260/940; 260/941; 260/972; 260/984; 424/212; 424/211
[58] Field of Search ........... 260/941, 940; 424/212, 424/210, 211

[56] References Cited

U.S. PATENT DOCUMENTS

| 3,760,040 | 9/1973 | Gutman | 260/941 |
| 3,784,589 | 1/1974 | Large | 260/941 |
| 3,975,523 | 8/1976 | Hoffman et al. | 260/941 X |

Primary Examiner—Anton H. Sutto
Attorney, Agent, or Firm—Robert J. Schwarz; Dietmar H. Olesch

[57] ABSTRACT

This invention discloses chemical compounds of the formula

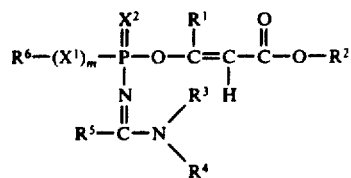

wherein $X^1$ and $X^2$ are independently selected from the group consisting of oxygen and sulfur; $m$ is the integer 0 or 1; $R^1$ is selected from the group consisting of hydrogen and alkyl; $R^2$ is alkyl; $R^3$ and $R^4$ are independently selected from the group consisting of hydrogen and alkyl; $R^5$ is selected from the group consisting of hydrogen, alkyl, alkoxy, alkylthio, amino and

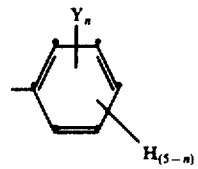

wherein Y is selected from the group consisting of alkyl, halogen, alkoxy, alkylthio, nitro and cyano; and $n$ is an integer from 0 to 3; and $R^6$ is selected from the group consisting of alkyl, alkenyl, alkoxyalkyl and

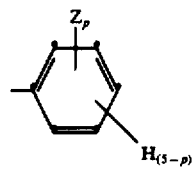

wherein Z is selected from the group consisting of alkyl, halogen, alkoxy, alkylthio, nitro and cyano; and $p$ is an integer from 0 to 3.

10 Claims, No Drawings

N-(α-AMINOALKYLIDENE)PHOSPHOR- AND PHOSPHONAMIDATES, AND METHOD FOR CONTROLLING INSECTS

This invention relates to new compositions of matter and more specifically relates to new chemical compounds of the formula

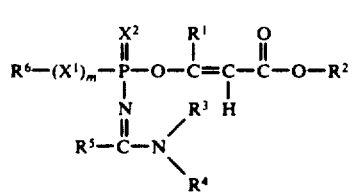
(I)

wherein $X^1$ and $X^2$ are independently selected from the group consisting of oxygen and sulfur; $m$ is the integer 0 or 1; $R^1$ is selected from the group consisting of hydrogen and alkyl; $R^2$ is alkyl; $R^3$ and $R^4$ are independently selected from the group consisting of hydrogen and alkyl; $R^5$ is selected from the group consisting of hydrogen, alkyl, alkoxy, alkylthio, amino and

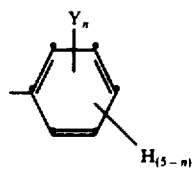

wherein Y is selected from the group consisting of alkyl, halogen, alkoxy, alkylthio, nitro and cyano; and $n$ is an integer from 0 to 3; and $R^6$ is selected from the group consisting of alkyl, alkenyl, alkoxyalkyl and

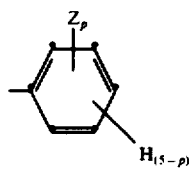

wherein Z is selected from the group consisting of alkyl, halogen, alkoxy, alkylthio, nitro and cyano; and $p$ is an integer from 0 to 3.

The compounds of the present invention are useful as insecticides.

In a preferred embodiment of the present invention $X^1$ and $X^2$ are independently selected from the group consisting of oxygen and sulfur; $m$ is the integer 0 or 1; $R^1$ is selected from the group consisting of hydrogen and lower alkyl; $R^2$ is lower alkyl; $R^3$ and $R^4$ are independently selected from the group consisting of hydrogen and lower alkyl; $R^5$ is selected from the group consisting of hydrogen, lower alkyl, lower alkoxy, lower alkylthio, amino and

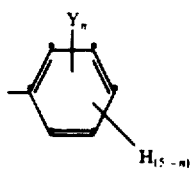

wherein Y is selected from the group consisting of lower alkyl, halogen, lower alkoxy, lower alkylthio, nitro and cyano; and $n$ is an integer from 0 to 3; and $R^6$ is selected from the group consisting of lower alkyl, lower alkenyl, lower alkoxyalkyl and

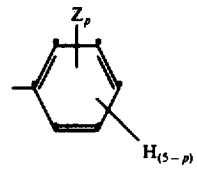

wherein Z is selected from the group consisting of lower alkyl, halogen, lower alkoxy, lower alkylthio, nitro and cyano; and $p$ is an integer from 0 to 3.

The term "lower" as used herein designates a straight or branched carbon chain of up to six carbon atoms.

The compounds of the present invention can be prepared by reacting a compound of the formula

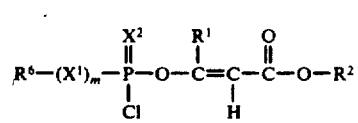
(II)

wherein $X^1$, $X^2$, $m$, $R^1$, $R^2$ and $R^6$ are as heretofore described, with a compound of the formula

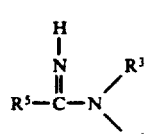
(III)

wherein $R^3$, $R^4$ and $R^5$ are as heretofore described. Typically the compounds of formula III are used in the form of their salts, such as the hydrochloride or the hydrogen sulfate. This reaction can be effected by combining the compounds of formulae II and III in an inert organic reaction medium, such as methylene chloride, at a temperature of about 5° C to about 40° C, followed by the incremental addition of aqueous inorganic base, such as an alkali metal hydroxide. A slight excess molar amount of the amidine hydrochloride and a large excess of base, such as 2 to 3 molar amounts based on the moles of the compound of formula II, can be used. After the addition of base is completed, the reaction mixture can be stirred for an additional period of up to about 4 hours to ensure completion of the reaction. After this time the desired product can be recovered from the organic phase upon removal of the solvent. The product can then be used as such or can be further purified by standard techniques well known in the art.

The compounds of formula II can be prepared by reacting a compound of the formula

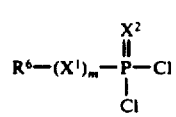
(IV)

wherein $X^1$, $X^2$, m and $R^6$ are as heretofore described, with an equimolar amount of a compound of the formula

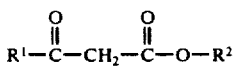 (V)

wherein $R^1$ and $R^2$ are as heretofore described. This reaction can be effected by combining the compounds of formulae IV and V in an inert organic reaction medium, such as benzene, and thereafter incrementally adding an equimolar or slight excess molar amount of an acid acceptor, such as a tertiary amine, with stirring at a temperature of from about 5° to about 40° C. After the addition is completed, stirring can be continued for a period of several hours to ensure completion of the reaction. After this time the reaction mixture can be filtered to remove the acid acceptor chloride that has formed. The remaining reaction mixture can then be stripped of solvent to yield the desired product. This product can be used as is or can be further purified by standard techniques practiced in the art.

The compounds of the present invention wherein $R^3$ and $R^4$ are alkyl can also be prepared by reacting a compound of the formula

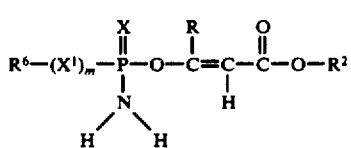 (VI)

wherein $X^1$, $X^2$, m, $R^1$, $R^2$ and $R^6$ are as heretofore described, with an N,N-dialkylformamide dimethylacetal of the formula

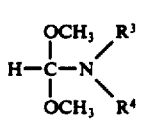 (VII)

wherein $R^3$ and $R^4$ are as heretofore described. This reaction can be effected by combining the compound of formula VI with a slight molar excess of the acetal of formula VII at room temperature with stirring. Typically a slight exotherm can be observed. After the exotherm has subsided, the reaction mixture can be heated at a temperature of up to about 80° C for a period of up to about 2 hours to ensure completion of the reaction. After this time the reacton mixture can be subjected to vacuum to remove unreacted starting material and volatile reaction side products, thereby yielding the desired product. This product can be used as such or can be further purified by conventional techniques in the art.

The compounds of formula VI can be prepared by reacting a compound of formula II, as heretofore described, with aqueous ammonia. This reaction can be effected by cooling a solution of the compound of formula II in an inert organic reaction medium, such as methylene chloride, to a temperature of from about 5° to about 20° C and thereafter incrementally adding concentrated aqueous ammonium hydroxide with vigorous stirring. After the addition is completed, stirring and cooling can be continued for a period of up to about one hour. After this time the reaction mixture can be allowed to warm to room temperature, and stirring can be continued for an additional period of up to 2 hours to ensure completion of the reaction. After this time the organic phase can be separated from the aqueous phase and washed with water. The washed solution can then be dried over anhydrous magnesium sulfate and filtered. The filtrate can then be stripped of solvent to yield the desired product as the residue. This product can be used as such or can be further purified by conventional means if desired.

Exemplary compounds of formula V useful for preparing the compounds of this invention are methyl acetylacetate, ethyl acetylacetate, propyl acetylacetate, butyl acetylacetate, pentyl acetylacetate, methyl propionylacetate, ethyl propionylacetate, propyl propionylacetate, methyl butanoylacetate, ethyl butanoylacetate, methyl pentanoylacetate, methyl hexanoylacetate, methyl heptanoylacetate, hexyl heptanoylacetate, methyl formylacetate, ethyl formylacetate, propyl formylacetate, butyl formylacetate and the like.

Exemplary compounds of formula IV useful for preparing the compounds of this invention are methylthionophosphonic dichloride, ethylthionophosphonic dichloride, propylthionophosphonic dichloride, phenylthionophosphonic dichloride, 2-methylphenylphosphonic dichloride, 4-chlorophenylphosphonic dichloride, 4-bromophenylphosphonic dichloride, 4-fluorophenylphosphonic dichloride, 3-iodophenylphosphonic dichloride, 2-methoxyphenylphosphonic dichloride, 3-methylthiophenylphosphonic dichloride, 3-nitrophenylphosphonic dichloride, 4-cyanophenylphosphonic dichloride, but-3-enylphosphonic dichloride, hex-4-enylphosphonic dichloride, 0-methyl thionophosphoric dichloride, 0-ethyl thionophosphoric dichloride, 0-propyl thionophosphoric dichloride, S-ethyl thionothiolophosphoric dichloride, S-butyl thionothiolophosphoric dichloride, S-hexyl thionothiolophosphoric dichloride, S-phenyl thionothiolophosphoric dichloride, S-(3,4-dichlorophenyl) thionothiolophosphoric dichloride, methoxymethylphosphonic dichloride, 0-methoxyethyl thionophosphoric dichloride, ethoxymethylthionophosphonic dichloride and the like.

Exemplary compounds of formula III useful for preparing the compounds of the present invention are guanidine, 0-methylisourea hydrogen sulfate, 0-ethylisourea hydrogen sulfate, S-methylisothiourea hydrogen sulfate, formamidine hydrochloride, acetamidine hydrochloride, benzamidine hydrochloride, 2-methylbenzamidine hydrochloride, 4-chlorobenzamidine hydrochloride, 3-methoxybenzamidine hydrochloride, 4-nitrobenzamidine hydrochloride, 4-cyanobenzamidine hydrochloride, propionamidine hydrochloride, butyramidine hydrochloride, pentanamidine hydrochloride, 0-propylisourea hydrogen sulfate, 0-butylisourea hydrogen sulfate, 0-pentylisourea hydrogen sulfate, S-ethylisothiourea hydrogen sulfate, S-propylisothiourea hydrogen sulfate, 0-methyl-N,N-dimethylisourea hydrogen sulfate and the like.

Exemplary compounds of formula VII useful for preparing the compounds of the present invention are N,N-dimethylformamide dimethylacetal, N,N-diethylformamide dimethylacetal, N,N-diproplformamide dimethylacetal, N,N-dibutylformamide dimethylacetal, N,N-dipentylformamide dimethylacetal, N,N-dihexylformamide dimethylacetal and the like.

The manner in which the compounds of the present invention can be prepared is more specifically illustrated in the following examples.

EXAMPLE 1

Preparation of O-(1-Methyl-2-methoxycarbonylvinyl) Ethylthionophosphonic Chloride

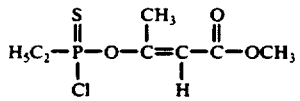

Ethylthionophosphonic dichloride (47.6 grams; 0.29 mole), methyl acetylacetate (33.6 grams; 0.29 mole) and benzene (100 ml) were charged into a glass reaction vessel equipped with a mechanical stirrer and thermometer. The reaction mixture was cooled to a temperature of about 10° C and triethylamine (29.3 grams; 0.29 mole) dissolved in benzene (20 ml) was added dropwise with vigorous stirring. After the addition was completed, the reaction mixture was allowed to warm to room temperature with continued stirring, resulting in the formation of a precipitate. The reaction mixture was then stirred for an additional period of about three hours at a temperature of from room temperature to about 45° C. After this time the reaction mixture was filtered to remove the triethylamine hydrochloride precipitate. The precipitate was washed with benzene, and the washings were combined with the filtrate. The combined solution was then stripped of solvent under reduced pressure to yield the desired product O-(1-methyl-2-methoxycarbonylvinyl) ethylthionophosphonic chloride as a pale yellow liquid.

EXAMPLE 2

Preparation of O-(1-Methyl-2-methoxycarbonylvinyl)N-(αAminoethylidene)ethylthionophosphonamidate

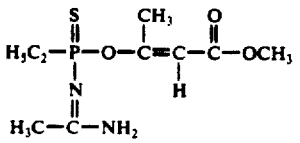

O-(1-Methyl-2-methoxycarbonylvinyl) ethylthionophosphonic chloride (4.84 grams; 0.02 mole), acetamidine hydrochloride (2.84 grams; 0.03 mole) and methylene chloride (50 ml) were charged into a glass reaction vessel equipped with a mechanical stirrer and thermometer. The mixture was cooled to a temperature of about 10° C, and a solution of sodium hydroxide (2.0 grams; 0.05 mole) in water (20 ml) was added dropwise with stirring. After the addition was completed, the reaction mixture was allowed to warm up to room temperature, and stirring was continued for a period of about 2 hours. After this time the organic phase was separated from the aqueous phase and was washed with water. The washed solution was then dried over anhydrous magnesium sulfate and was filtered. The filtrate was stripped of solvent under reduced pressure, leaving an oil. This oil was allowed to stand under vacuum for a period of about 1 hour to yield the desired product O-(1-methyl-2-methoxycarbonylvinyl) N-(αaminoethylidene)ethylthionophosphonamidate.

EXAMPLE 3

Preparation of O-(1-Methyl-2-isopropoxycarbonylvinyl)Ethylthionophosphonic Chloride

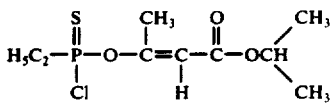

Isopropyl acetylacetate (41.7 grams; 0.29 mole) and benzene (100 ml) were charged into a glass reaction vessel equipped with a mechanical stirrer and thermometer. The mixture was cooled to a temperature of about 10° C, and ethylthionophosphonic dichloride (47.6 grams; 0.25 mole) was added thereto. The mixture was then stirred vigorously, and a solution of triethylamine (29.3 gram; 0.29 mole) in benzene (25 ml) was added dropwise over a period of about 60 minutes. After the addition was completed, stirring was continued while maintaining the temperature of the reaction mixture at about 10° C for a period of about 30 minutes. After this time the temperature of the mixture was allowed to rise to about 15° C for a period of about 60 minutes. The mixture was thereafter warmed to room temperature and stirred for an additional 60 minutes and to about 45° C for about 2 hours. After this time the reaction mixture was filtered to remove triethylamine salt which formed as a precipitate. The filtrate was then dissolved in ether, resulting in additional precipitation of triethylamine salt. The mixture was again filtered and the filtrate stripped of solvents in a rotary evaporator under reduced pressure. The residue was subjected to distillation in a one foot Vigreaux column to yield the desired product O-(1-methyl-2-isopropoxycarbonylvinyl) ethylthionophosphonic chloride.

EXAMPLE 4

Preparation of O-(1-Methyl-2-isopropoxycarbonylvinyl)N-(αAminoethylidene)ethylthionophosphonamidate

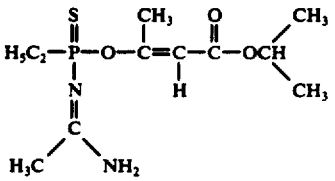

O-(1-Methyl-2-isopropoxycarbonylvinyl) ethylthionophosphonic chloride (5.41 grams; 0.02 mole), methylene chloride (60 ml) and acetamidine hydrochloride were charged into a glass reaction vessel equipped with a mechanical stirrer and thermometer. The mixture was cooled to a temperature of about 10° C, and a solution of sodium hydroxide (2.0 grams; 0.05 mole) in water 20 ml) was added dropwise with vigorous stirring. After the addition was completed, the reaction mixture was stirred at room temperature for a period of about 18 hours. After this time the organic phase was separated from the aqueous phase and was washed with water. The washed solution was dired over anhydrous magnesium sulfate and filtered. The filtrate was then stripped of solvent under reduced pressure, leaving an oil as the residue. This oil was let stand under vacuum (0.20 mm of Hg) for a period of about 1 hour to yield the desired product O-(1-methyl-2-isopropoxycarbonylvinyl) N-(α-aminoethylidene)ethylthionophosphonamidate as a yellow viscous oil.

EXAMPLE 5

Preparation of
O-(1-Methyl-2-isopropoxycarbonylvinyl)
N-(α-Aminobenzylidene)ethylthionophosphonamidate

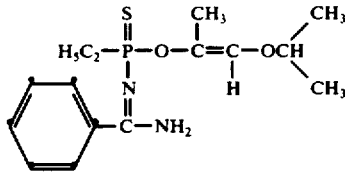

O-(1-Methyl-2-isopropoxycarbonylvinyl) ethylthionophosphonic chloride (5.41 grams; 0.02 mole), benzamidine hydrochloride (4.70 grams; 0.03 mole) and methyl chloride (60 ml) were charged into a glass reaction vessel equipped with a mechanical stirrer and thermometer. The mixture was cooled to a temperature of about 5° C, and a solution of sodium hydroxide (2.0 grams; 0.05 mole) in water (20 ml) was added dropwise with stirring. After the addition was completed, stirring was continued at 5° to 10° C for a period of one hour. After this time the reaction mixture was allowed to warm up to room temperature, and stirring was continued for a period of about 10 hours. After this time the organic phase was separated from the aqueous phase and was washed with water. The washed solution was then dried over anhydrous magnesium sulfate and was filtered. The filtrate was stripped of solvent under reduced pressure, leaving an oil. This oil was allowed to stand under vacuum for a period of about 5 minutes to yield the desired product O-(1-methyl-2-isopropoxycarbonylvinyl) N-(α-aminobenzylidene)ethylthionophosphonamidate as a pale yellow oil.

EXAMPLE 6

Preparation of
O-(1-Methyl-2-isopropoxycarbonylvinyl)
N-(α-Amino-α-methoxymethylidene)ethylthionophosphonamidate

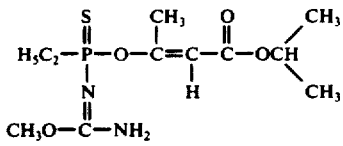

O-(1-Methyl-2-isopropoxycarbonylvinyl) ethylthionophosphonic chloride (5.41 grams; 0.02 moles) and methylene chloride (60ml) were charged into a glass reaction vessel equipped with a mechanical stirrer and thermometer. The mixture was cooled to a temperature of about 5° C, and O-methylisourea (5.16 grams; 0.03 mole) was added. The mixture was stirred, and a solution of sodium hydroxide (2.0 grams; 0.05 mole) in water (20 ml) was added dropwise. After the addition was completed, the reaction mixture was stirred for a period of about 1 hour. After this time the mixture was allowed to warm up to room temperature, and stirring was continued for a period of about 16 hours. After this time the organic phase was separated from the aqueous phase and was washed with water. The washed solution was then dried over anhydrous magnesium sulfate and was filtered. The filtrate was stripped of solvent under reduced pressure, leaving an oil. This oil was allowed to stand under vacuum for a period of about 1 hour to yield the desired product O-(1-methyl-2-isopropoxycarbonylvinyl) N-(α-amino-α-methoxymethylidene)ethylthionophosphonamidate as a yellow oil.

EXAMPLE 7

Preparation of
O-(1-Methyl-2-isopropoxycarbonylvinyl)
N-(Aminomethylidene)ethylthionophosphonamidate

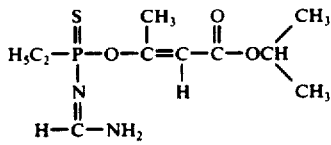

O-(1-Methyl-2-isopropoxycarbonylvinyl) ethylthionophosphonic chloride (5.41 grams; 0.02 mole), formamidine acetate (2.84 grams; 0.03 mole) and methylene chloride (60 ml) were charged into a glass reaction vessel equipped with a mechanical stirrer and thermometer. The mixture was cooled to a temperature of 5° to 10° C, and a solution of sodium hydroxide (2.0 grams; 0.05 mole) in water (20 ml) was added dropwise with stirring. After the addition was completed, stirring was continued at 5° to 10° C for a period of about 60 minutes. After this time the reaction mixture was allowed to warm up to room temperature and was stirred for a period of about 7 hours. The organic phase was then separated from the aqueous phase and was washed with water. The washed solution was then dried over anhydrous magnesium sulfate and filtered. The filtrate was stripped of solvent under reduced pressure, leaving an oil. This oil was allowed to stand under vacuum at 45° C for a period of about 5 minute to yield the desired product O-(1-methyl-2-isopropoxycarbonylvinyl) N-(aminomethylidene)ethylthionophosphonamidate as a pale yellow oil.

EXAMPLE 8

Preparation of
O-(1-Methyl-2-isopropoxycarbonylvinyl)
N-(α-Amino-α-methylthiomethylidene)ethylthionophosphonamidate

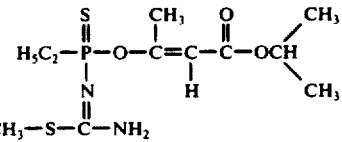

O-(1-Methyl-2-isopropoxycarbonylvinyl) ethylthionophosphonic chloride (5.41 grams; 0.02 mole) and methylene chloride (60 ml) were charged into a glass reaction vessel equipped with a mechanical stirrer and thermometer. The mixture was cooled to a temperature of about 5° C, and S-methylisothiourea hydrogen iodide (6.54 grams; 0.03 mole) was added. A solution of sodium hydroxide (2.0 grams; 0.05 mole) in water (20 ml) was thereafter added dropwise, and the mixture was stirred at about 10° C for a period of about 60 minutes. The reaction mixture was allowed to warm up to room temperature, and stirring was continued for a period of about 8 hours. After this time the organic phase was separated from the aqueous phase and washed with water. The washed solution was then dried over anhydrous magnesium sulfate and filtered. The filtrate was stripped of solvent under reduced pressure, leaving an oil. This oil was allowed to stand under vacuum at 45° C for a period of about 5 minutes to yield the desired product O-(1-methyl-2-isopropoxycarbonylvinyl) N-(α-amino-α-methylthiomethylidene)ethylthionophosphonamidate as an oil.

EXAMPLE 9

Preparation of O-(1-Methyl-2-methoxycarbonylvinyl) N-(Aminomethylidene)ethylthionophosphonamidate

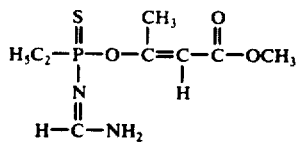

O-(1-Methyl-2-methoxycarbonylvinyl) ethylthionophosphonic chloride (4.85 grams; 0.02 mole) and methyleme chloride (60 ml) were charged into a glass reaction vessel equipped with a mechanical stirrer and thermometer. The mixture was cooled to a temperature of about 10° C, and formamidine acetate (3.12 grams; 0.03 mole) was added thereto. This mixture was stirred, and a solution of sodium hydroxide (2.0 grams; 0.05 mole) in water (25 ml) was added dropwise thereto. After the addition was completed, stirring and cooling were continued for about 30 minutes. The reaction mixture was then allowed to warm up to room temperature, and stirring was continued for a period of about 16 hours. After this time the organic phase was separated from the aqueous phase and washed with water. The washed solution was then dried over anhydrous magnesium sulfate and was filtered. The filrate was stripped of solvent under reduced pressure, leaving an oil. This oil was allowed to stand under vacuum at 50° C for a period of about 5 minutes to yield the desired product O-(1-methyl-2-methoxycarbonylvinyl) N-(aminomethylidene)-ethylthionophosphonamidate as a pale yellow oil.

EXAMPLE 10

Preparation of O-(1-Methyl-2-methoxycarbonylvinyl) N-(α-Amino-α-methoxymethylidene)ethylthionophosphonamidate

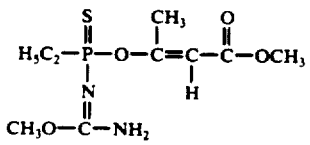

O-(1-Methyl-2-methoxycarbonylvinyl) ethylthionophosphonic chloride (4.85 grams; 0.02 mole) and methylene chloride (60 ml) were charged into a glass reaction vessel equipped with a mechanical stirrer and thermometer. The mixture was cooled to a temperature of about 10° C, and O-methylisourea hydrogen sulfate (6.88 grams; 0.04 mole) was added. A solution of sodium hydroxide (2.4 grams; 0.06 mole) in water (25 ml) was then added dropwise with stirring. After the addition was completed, stirring and cooling were continued for about 30 minutes. The reaction mixture was then allowed to warm up to room temperature and stirred for an additional period of about 10 hours. After this time the organic phase was separated from the aqueous phase and washed with water. The washed solution was then dried over anhydrous magnesium sulfate and filtered. The filtrate was stripped of solvent under reduced pressure, leaving an oil. This oil was allowed to stand under vacuum at 50° C for a period of about 5 minutes to yield the desired product O-(1-methyl-2-methoxycarbonylvinyl) N-(α-amino-α-methoxymethylidene)-ethylthionophosphonamidate as a pale yellow oil.

EXAMPLE 11

Preparation of O-(1-Methyl-2-methoxycarbonylvinyl) N-(α-Amino-α-methylthiomethylidene)ethylthionophosphonamidate

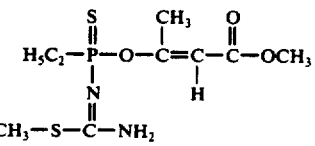

O-(1-Methyl-2-methoxycarbonylvinyl) ethylthionophosphonic chloride (4.85 grams; 0.02 mole) and methylene chloride (60 ml) were charged into a glass reaction vessel equipped with a mechanical stirrer and thermometer. The mixture was cooled to a temperature of about 10° C, and S-methylisothiourea hydrogen iodide (6.54 grams; 0.03 mole) was added. A solution of sodium hydroxide (2.0 grams; 0.05 mole) in water (25 ml) was then added dropwise with stirring. After the addition was completed, stirring and cooling were continued for about 30 minutes. The reaction mixture was then allowed to warm up to room temperature, and stirring was continued for a period of about 10 hours. After this time the organic phase was separated from the aqueous phase and washed with water. The washed solution was then dried over anhydrous magnesium sulfate and filtered. The filtrate was stripped of solvent under reduced pressure, leaving an oil. This oil was allowed to stand under vacuum at 50° C for a period of about 5 minutes to yield the desired product O-(1-methyl-2-methoxycarbonylvinyl) N-(α-amino- α -methylthiomethylidene)-ethylthionophosphonamidate as a pale yellow oil.

EXAMPLE 12

Preparation of O-(1-Methyl-2-isopropoxycarbonylvinyl) N-(α,α-Diaminomethylidene)ethylthionophosphonamidate

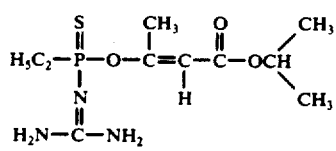

O-(1-Methyl-2-isopropoxycarbonylvinyl) ethylthionophosphonic chloride (5.41 grams; 0.02 mole) and methylene chloride (65 ml) were charged into a glass reaction vessel equipped with a mechanical stirrer and thermometer. The mixture was cooled to a temperature of about 10° C, and guanidine hydrochloride (2.96 grams; 0.03 mole) was added. A solution of sodium hydroxide (2.0 grams; 0.05 mole) in water (20 ml) was then added dropwise with stirring. After the addition was completed, stirring and cooling were continued for about 30 minutes. The reaction mixture was then allowed to warm up to room temperature and stirred for an additional period of about 8 hours. After this time the organic phase was separated from the aqueous phase and washed with water. The washed solution was then dried over anhydrous magnesium sulfate and filtered. The filtrate was stripped of solvent under reduced pressure, leaving an oil. This oil was allowed to stand under vacuum at 50° C for a period of several minutes, causing it to solidify. This solid was triturated in hexane and dried under vacuum to yield the desired product O-(1-methyl-2-isopropoxycarbonylvinyl) N-(α,α-diaminomethylidene)-ethylthionophosphonamidate as a white solid melting at 95° to 99° C.

EXAMPLE 13

Preparation of O-(1-Ethyl-2-ethoxycarbonylvinyl) O-Ethyl Phosphoric Chloride

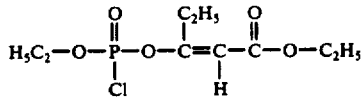

O-Ethyl phosphoric dichloride (0.3 mole), ethyl propionylacetate (0.3 mole) and benezene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined soluton is then stripped of solvent to yield the desired product O-(1-ethyl-2-ethoxycarbonylvinyl) O-ethyl phosphoric chloride as the residue.

EXAMPLE 14

Preparation of 0-(1-Ethyl-2-ethoxycarbonylvinyl) O-Ethyl N-(α-Amino-2-methylbenzylidene)phosphoramidate

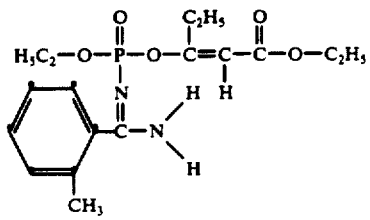

O-(1-Ethyl-2-ethoxycarbonylvinyl) O-ethyl phosphoric chloride (0.02 mole) and methylene chloride (25 ml) are charged into a glass reaction vessel equipped with a mechanical stirrer and thermometer. The mixture is cooled to a temperature of about 5° C, and 2-methylbenzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-ethyl-2-ethoxycarbonylvinyl) O-ethyl N-(α-amino-2-methylbenzylidene)phosphoramidate as the residue.

EXAMPLE 15

Preparation of O-(1-Ethyl-2-methoxycarbonylvinyl) S-(4-Methylphenyl) Thionothiolophosphoric Chloride

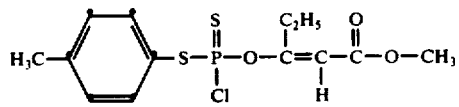

S-(4-Methylphenyl) thionothiolophosphoric dichloride (0.03 mole), methyl propionylacetate (0.03 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvent to yield the desired product O-(1-ethyl-2-methoxycarbonylvinyl) S-(4-methylphenyl) thionothiolophosphoric chloride as the residue.

EXAMPLE 16

Preparation of O-(1-Ethyl-2-methoxycarbonylvinyl) S-(4-Methylphenyl) N-(α-Amino-3,4-dichlorobenzylidene)thionothiolophosphoramidate

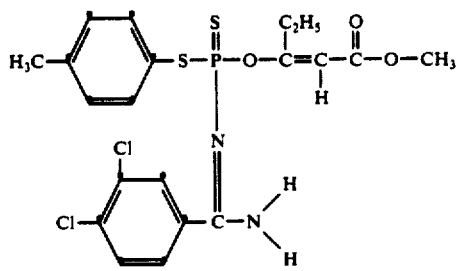

O-(1-Ethyl-2-methoxycarbonylvinyl) S-(4-methylphenyl) thionothiolophosphoric chloride (0.02 mole) and methylene chloride (25 ml) are charged into a glass reaction vessel equipped with a mechanical stirrer and thermometer. The mixture is cooled to a temperature of about 5° C, and 3,4-dichlorobenzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1ethyl-2-methoxycarbonylvinyl) S-(4-methylphenyl) N-(α-amino-3,4-dichlorobenzylidene)thionothiolophosphoramidate as the residue.

EXAMPLE 17

Preparation of O-(1-Methyl-2-methoxycarbonylvinyl) O-(2-Methoxyphenyl) Thionophosphoric Chloride

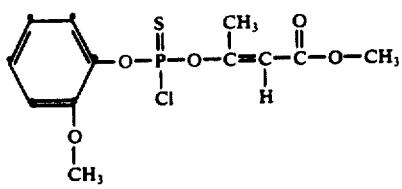

O-(2-Methoxyphenyl) thionophosphoric dichloride (0.3 mole), methyl acetylacetate (0.03 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvent to yield the desired product O-(1-methyl-2-methyoxycarbonylvinyl) O-(2-methoxyphenyl) thionophosphoric chloride as the residue.

EXAMPLE 18

Preparation of O-(1-Methyl-2-methoxycarbonylvinyl) O-(2-Methoxyphenyl) N-(α-Amino-α-ethylthiomethylene)thionophosphoramidate

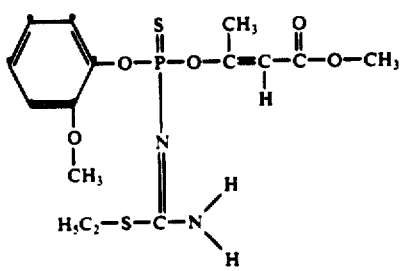

O-(1-Methyl-2-methoxycarbonylvinyl) O-(2-methoxyphenyl) thionophosphoric chloride (0.02 mole) and methylene chloride (25 ml) are charged into a glass reaction vessel equipped with a mechanical stirrer and thermometer. The mixture is cooled to a temperature of about 5° C, and S-ethylisothiourea hydrogen sulfate (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-methyl-2-methoxycarbonylvinyl) O-(2-methoxyphenyl) N-(α-amino-α-ethylthiomethylene)thionophosphoramidate as the residue.

EXAMPLE 19

Preparation of O-(1-Methyl-2-methoxycarbonylvinyl) 4-Bromophenylthionophosphonic Chloride

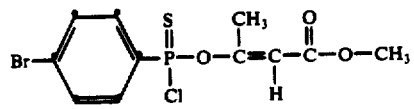

4-Bromophenylthionophosphonic dichloride (0.3 mole), methyl acetylacetate (0.3 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvents to yield the desired product O-(1-methyl-2-methoxycarbonylvinyl) 4-bromophenylthionophosphonic chloride as the residue.

EXAMPLE 20

Preparation of O-(1-Methyl-2-methoxycarbonylvinyl) N-(α-Amino-4-methylthiobenzylidene)-4-bromophenylthionophosphonamidate

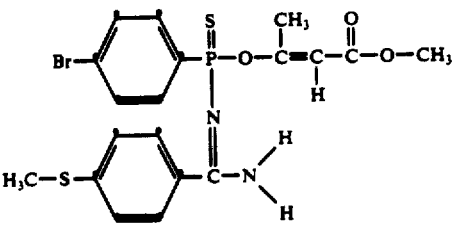

O-(1-Methyl-2-methoxycarbonylvinyl) 4-bromophenylthionophosphonic chloride (0.02 mole) and methylene chloride (25 ml) are charged into a glass reaction vessel equipped with a mechanical stirrer and thermometer. The mixture is cooled to a temperature of about 5° C, and 4-methylthiobenzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-methyl-2-methoxycarbonylvinyl) N-(α-amino-4-methylthiobenzylidene)-4-bromophenylthionophosphonamidate as the residue.

EXAMPLE 21

Preparation of O-(1-Methyl-2-t-butyloxycarbonylvinyl) O-(3,4-Dinitrophenyl) Phosphoric Chloride

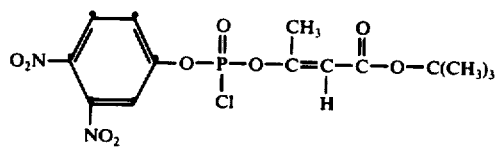

O-(3,4-Dinitrophenyl) phosphoric dichloride (0.3 mole), t-butyl acetylacetate (0.03 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvent to yield the desired product O-(1-methyl-2-t-butyloxycarbonylvinyl) O-(3,4-dinitrophenyl) phosphoric chloride as the residue.

EXAMPLE 22

Preparation of O-(1-Methyl-2-t-butyloxycarbonylvinyl) O-(3,4-Dinitrophenyl) N-(α-Amino-4-cyanobenzylidene)phosphoramidate

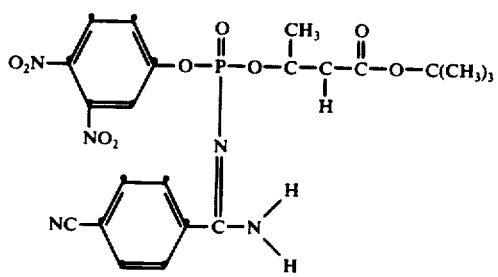

O-(1-Methyl-2-t-butyloxycarbonylvinyl) O-(3,4-dinitrophenyl) phosphoric chloride (0.02 mole) and methylene chloride (25 ml) are charged into a glass reaction vessel equipped with a mechanical stirrer and thermometer. The mixture is cooled to a temperature of about 5° C, and 4-cyanobenzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-methyl-2-t-butyloxycarbonylvinyl) O-(3,4-dinitrophenyl) N-(α-amino-4-cyanobenzylidene)phosphoramidate as the residue.

EXAMPLE 23

Preparation of O-(1-Methyl-2-methoxycarbonylvinyl) 4-Methylthiophenylthionophosphonic Chloride

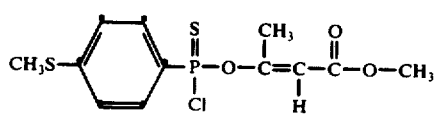

4-Methylthiophenylphosphonic dichloride (0.3 mole), methyl acetylacetate (0.3 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvent to yield the desired product O-(1-methyl-2-methoxycarbonylvinyl) 4-methylthiophenylthionophosphonic chloride as the residue.

EXAMPLE 24

Preparation of O-(1-Methyl-2-methoxycarbonylvinyl) N-(α-Amino-3-nitrobenzylidene)-4-methylthiophenylthionophosphonamidate

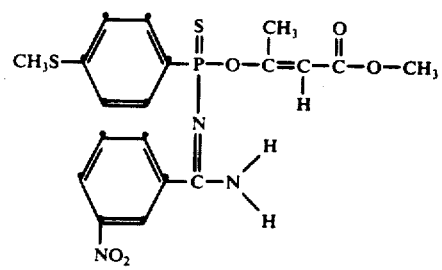

O-(1-Methyl-2-methoxycarbonylvinyl) 4-methylthiophenylthionophosphonic chloride (0.02 mole) and methylene chloride (25 ml) are charged into a glass reaction vessel equipped with a mechanical stirrer and thermometer. The mixture is cooled to a temperature of about 5° C, and 3-nitrobenzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-methyl-2-methoxycarbonylvinyl) N-(α-amino-3-nitrobenzylidene)-4-methylthiophenylthionophosphonamidate as the residue.

EXAMPLE 25

Preparation of O-(1-Methyl-2-methoxycarbonylvinyl) 4-Cyanophenylthionophosphonic Chloride

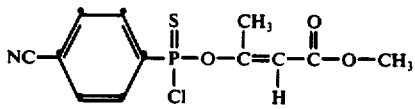

4-Cyanophenylthionophosphonic dichloride (0.3 mole), methyl acetylacetate (0.3 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvent to yield the desired product O-(1-methyl-2-methoxycarbonylvinyl) 4-cyanophenylthionophosphonic chloride as the residue.

EXAMPLE 26

Preparation of O-(1-Methyl-2-methoxycarbonylvinyl) N-(α-Amino-2-methoxybenzylidene)-4-cyanophenylthionophosphonamidate

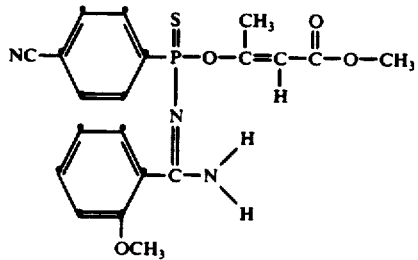

O-(1-Methyl-2-methoxycarbonylvinyl) 4-cyanophenylthionophosphonic chloride (0.02 mole) and methylene chloride (25 ml) are charged into a glass reaction vessel equipped with a mechanical stirrer and thermometer. The mixture is cooled to a temperature of about 5° C, and 2-methoxybenzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-methyl-2-methoxycarbonylvinyl) N-(α-amino-2-methoxybenzylidene)-4-cyanophenylthionophosphonamidate as the residue.

EXAMPLE 27

Preparation of O-(1-Propyl-2-methoxycarbonylvinyl) Allylthionophosphonic Chloride

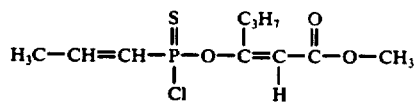

Allylthionophosphonic dichloride (0.3 mole), methyl butanoylacetate (0.3 mole) and benzene (100 ml) are charged into a glass reaction vessel equipped with a mechanical stirrer and thermometer. The reaction mixture is cooled to a temperature of about 10° C, and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvents to yield the desired product O-(1-propyl-2-methoxycarbonylvinyl) allylthionophosphonic chloride as the residue.

EXAMPLE 28

Preparation of O-(1-Methyl-2-methoxycarbonylvinyl) Ethylthionophosphonamidate

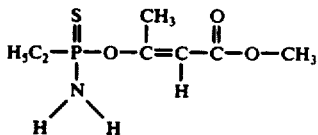

O-(1-Methyl-2-methoxycarbonylvinyl) ethylthionophosphonic chloride (8.47 grams; 0.035 mole) and methylene chloride (60 ml) were charged into a glass reaction vessel equipped with a thermometer and mechanical stirrer. The reaction mixture was cooled to a temperature of about 10° C, and concentrated aqueous ammonium hydroxide (10 ml ) was added dropwise with stirring. After the addition was completed, stirring and cooling were continued for a period of about 30 minutes. After this time the reaction mixture was allowed to warm to room temperature, and stirring was continued for an additional period of about 45 minutes. The organic phase was then separated from the aqueous phase and washed with water. The washed solution was dried over anhydrous magnesium sulfate and filtered. The filtrate was then stripped of solvent, leaving a residue. This residue was allowed to stand under vacuum at 50° C for several minutes to yield the desired product O-(1-methyl-2-methoxycarbonylvinyl) ethylthionophosphonamidate as an oil.

EXAMPLE 29

Preparation of O-(1-Methyl-2-methoxycarbonylvinyl) N-(α-Dimethylaminomethylidene)ethylthionophosphonamidate

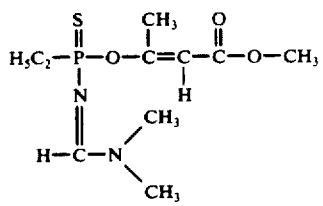

O-(1-Methyl-2 1-methoxycarbonylvinyl) ethylthionophosphonamidate (6.0 grams; 0.027 mole) and N,N-dimethylformamide dimethylacetal (4.52 grams; 0.038 mole) were charged into a glass reaction vessel equipped with a magnetic stirrer and thermometer. The reaction mixture was stirred, and an exotherm raised the reaction temperature to 35° C. After the exotherm subsided, the reaction mixture was heated at a temperature of 70° C for a period of about 1 hour. After this time the mixture was subjected to vacuum to remove volatiles and to yield the desired product O-(1-methyl-2-methoxycarbonylvinyl) N-(α-dimethylaminomethylidene)ethylthionophosphonamidate as an amber oil.

EXAMPLE 30

Preparation of O-(1-Methyl-2-methoxycarbonylvinyl) S-Ethyl Thiolothionophosphoramidate

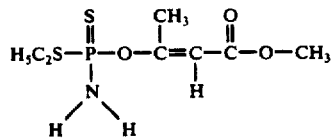

O-(1-Methyl-2-methoxycarbonylvinyl) S-ethyl thiolothionophosphoric chloride (0.035 mole) and methyl chloride are charged into a glass reaction vessel equipped with a mechanical stirrer and thermometer. The reaction mixture is cooled to a temperature of about 10° C, and concentrated aqueous ammonium hydroxide (10 ml) is added dropwise with stirring. After the addition is completed, stirring and cooling are continued for a period of about 30 minutes. The reaction mixture is then allowed to warm up to room temperature, and stirring is continued for an additional period of about 45 minutes. After this time the organic phase is separated from the aqueous phase and washed with water. The washed solution is dried over anhydrous magnesium sulfate and filtered. The filtrate is then stripped of solvent, leaving a residue. The residue is allowed to stand under vacuum at 50° C for several minutes to yield the desired product O-(1-methyl-2-methoxycarbonylvinyl) S-ethyl thiolothionophosphoramidate.

EXAMPLE 31

Preparation of O-(1-Methyl-2-methoxycarbonylvinyl) S-Ethyl N-(α-Diethylaminomethylidene)-thiolothionophosphoramidate

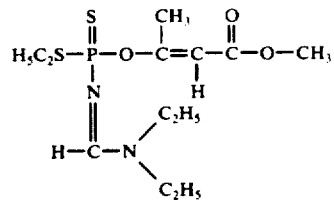

O-(1-Methyl-2-methoxycarbonylvinyl) S-ethyl thiolothionophosphoramidate (0.03 mole) and N,N-diethylformamide dimethylacetal (0.04 mole) are charged into a glass reaction vessel equipped with a magnetic stirrer and thermometer. The reaction mixture is stirred until any exotherm has subsided. After this time the mixture is heated at 70° C with stirring for an additional period of about one hour. The mixture is then subjected to vacuum to yield the desired product O-(1-methyl-2-methoxycarbonylvinyl) S-ethyl N-(α-diethylaminomethylidene)thiolothionophosphoramidate.

EXAMPLE 32

Preparation of O-(1-Methyl-2-methoxycarbonylvinyl) β-Methoxyethylthionophosphonic Chloride

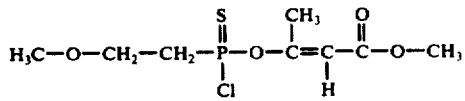

Methyl acetylacetate (0.3 mole), β-methoxyethylthionophosphonic dichloride (0.3 mole) and benzene (100 ml) are charged into a glass reaction vessel equipped with a mechanical stirrer and thermometer. The reaction mixture is cooled to a temperature of about 10° C and triethylamine (30 grams; 0.3 mole) dissolved in benzene (25 ml) is added dropwise with vigorous stirring. After the addition is completed, the reaction mixture is allowed to warm to room temperature, and stirring is continued for a period of about 3 hours. The reaction mixture is thereafter stirred at a temperature of about 45° C for a period of about 1 hour. After this time the reaction mixture is filtered to remove triethylamine hydrochloride salt that has formed. This salt is washed with benzene, and the washings are combined with the filtrate. The combined solution is then stripped of solvent to yield the desired product O-(1-methyl-2-methoxycarbonylvinyl) β-methoxyethylthionophosphonic chloride as the residue.

EXAMPLE 33

Preparation of O-(1-Methyl-2-methoxycarbonylvinyl) N-(α-Aminobenzylidene)-β-methoxyethylthionophosphonamidate

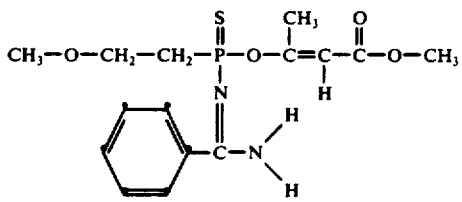

O-(1-Methyl-2-methoxycarbonylvinyl) β-methoxyethylthionophosphonic chloride (0.02 mole) and methylene chloride (25 ml) are charged with a glass reaction vessel equipped with a mechanical stirrer and thermometer. The mixture is cooled to a temperature of about 5° C, and benzamidine hydrochloride (0.03 mole) is added thereto. A solution of sodium hydroxide (2.0 grams; 0.02 mole) in water (20 ml) is then added dropwise with vigorous stirring. After the addition is completed, stirring and cooling are continued for a period of about one hour. After this time the reaction mixture is allowed to warm to room temperature and is stirred for an additional period of about 12 hours. The organic phase is then separated from the aqueous phase and washed with water. The washed solution is dried over anhydrous magnesium sulfate and filtered. The filtrate is stripped of solvent under reduced pressure to yield the desired product O-(1-methyl-2-methoxycarbonylvinyl) N-(α-aminobenzylidene)-β-methoxyethylthionophosphonamidate as the residue.

Additional compounds within the scope of this invention which can be prepared according to the procedures detailed in the foregoing examples include O-(1-methyl-2-methoxycarbonylvinyl) O-butyl N-(α-aminopropylidene)thionophosphoramidate, O-(1-ethyl-2-propoxycarbonylvinyl) O-propyl N-(α-aminobutylidene)thionophosphoramidate, O-(1-propyl-2-butoxycarbonylvinyl) O-methyl N-(α-aminopentylidene)thionophosphoramidate, O-(1-pentyl-2-hexyloxycarbonylvinyl) O-hexyl N-(α-aminohexylidene)thionophosphoramidate, O-(1-hexyl-2-methoxycarbonylvinyl) O-but-3-enyl N-(α-aminoheptylidene)thionophosphoramidate, O-(1-methyl-2-methoxycarbonylvinyl) O-pent-4-enyl N-(α-diethylaminoethylidene)thionophosphoramidate, O-(1-methyl-2-methoxycarbonylvinyl) O-hex-4-enyl N-(α-dipropylaminoethylidene)thionophosphoramidate, O-(1-methyl-2-methoxycarbonylvinyl) O-(2-ethylphenyl) N-(α-dibutylaminoethylidene)thionophosphoramidate, O-(1-methyl-2-methoxycarbonylvinyl) O-(2-propylphenyl) N-(α-dihexylaminoethylidene)thionophosphoramidate, O-(1-methyl-2-methoxycarbonylvinyl) O-(3-butylphenyl) N-(α-amino-α-ethoxyethylidene)thionophosphoramidate, O-(1-methyl-2-methoxycarbonylvinyl) O-(4-hexylphenyl) N-(α-amino-α-propoxyethylidene)thionophosphoramidate, O-(1-methyl-2-methoxycarbonylvinyl) O-(4-chlorophenyl) N-(α-amino-α-butoxyethylidene)thionophosphoramidate, O-(1-methyl-2-methoxycarbonylvinyl) O-(3,4-dichlorophenyl) N-(α-amino-α-hexyloxyethylidene)thionophosphoramidate, O-(1-methyl-2-methoxycarbonylvinyl) O-(4-iodophenyl) N-(α-amino-α-ethylthioethylidene)thionophosphoramidate, O-(1-methyl-2-methoxycarbonylvinyl) O-(4-fluorophenyl) N-(α-amino-α-propylthioethylidene)thionophosphoramidate, O-(1-methyl-2-methoxycarbonylvinyl) O-(2-ethoxyphenyl) N-(α-amino-α-butylthioethylidene)thionophosphoramidate, O-(1-methyl-2-methoxycarbonylvinyl) O-(2-propoxyphenyl) N-(α-amino-α-hexylthioethylidene)thionophosphoramidate, O-(1-methyl-2-methoxycarbonylvinyl) S-(4-butyloxyphenyl) N-(α-aminoethylidene)thionophosphoramidate, O-(1-methyl-2-methoxycarbonylvinyl) S-(4-hexyloxyphenyl) N-(α-aminoethylidene)thionophosphoramidate, O-(1-methyl-2-methoxycarbonylvinyl) S-(4-ethylthiophenyl) N-(α-aminoethylidene)thionothiolophosphoramidate, O-(1-methyl-2-methoxycarbonylvinyl) S-(4-butylthiophenyl) N-(α-aminoethylidene)thionothiolophosphoramidate, O-(1-methyl-2-methoxycarbonylvinyl) S-(4-hexylthiophenyl) N-(α-aminoethylidene)thionothiolophosphoramidate, O-(1-methyl-2-methoxycarbonylvinyl) S-(3,4,5-trichlorophenyl) N-(α-aminoethylidene)thionothiolophosphoramidate, O-(1-methyl-2-methoxycarbonylvinyl) S-(2-methyl-4-chlorophenyl) N-(α-aminoethylidene)thionothiolophosphoramidate, O-(1-methyl-2-methoxycarbonylvinyl) N-(α-amino-2-ethylbenzylidene)ethylthionophosphonamidate, O-(1-methyl-2-methoxycarbonylvinyl) N-(α-amino-2-propylbenzylidene)isopropylthionophosphonamidate, O-(1-methyl-2-methoxycarbonylvinyl) N-(α-amino-2-butylbenzylidene)phenylthionophosphonamidate, O-(1-methyl-2-methoxycarbonylvinyl) N-(α-amino-2-hexylbenzylidene)phenylthionophosphonamidate, O-(1-methyl-2-methoxycarbonylvinyl) N-(α-amino-4-bromobenzylidene)phenylthionophosphonamidate, O-(1-methyl-2-methoxycarbonylvinyl) N-(α-amino-4-chlorobenzylidene)phenylthionophosphonamidate, O-(1-methyl-2-methoxycarbonylvinyl) N-(α-amino-4-iodobenzylidene)phenylthionophosphonamidate, O-(1-methyl-2-methoxycarbonylvinyl) N-(α-amino-4-fluorobenzylidene)phenylthionophosphonamidate, O-(1-methyl-2-methoxycarbonylvinyl) N-(α-amino-2-methoxybenzylidene)phenylthionophosphonamidate, O-(1-methyl-2-methoxycarbonylvinyl) N-(α-amino-3-ethoxybenzylidene)phenylthionophosphonamidate, O-(1-methyl-2-methoxycarbonylvinyl) N-(α-amino-4-propoxybenzylidene)phenylthionophosphonamidate, O-(1-methyl-2-methoxycarbonylvinyl) N-(α-amino-4-hexyloxybenzylidene)phenylthionophosphonamidate, O-(1-methyl-2-methoxycarbonylvinyl) N-(α-amino-4-ethylthiobenzylidene)ethylphosphonamidate, O-(1-methyl-2-methoxycarbonylvinyl) N-(α-amino-4-propylthiobenzylidene)ethylphosphonamidate, O-(1-methyl-2-methoxycarbonylvinyl) N-(α-amino-3-butylthiobenzylidene)ethylphosphonamidate, O-(1-methyl-2-methoxycarbonylvinyl) N-(α-amino-4-hexylthiobenzylidene)ethylphosphonamidate, O-(1-methyl-2-methoxycarbonylvinyl) N-(α-amino-2-methyl-4-chlorobenzylidene)-4-chlorophenylphosphonamidate, O-(1-methyl-2-methoxycarbonylvinyl) N-(α-amino-3,4,5-trichlorobenzylidene)-2-methylphenylphosphonamidate, O-(1-methyl-2-methoxycarbonylvinyl) N-(α-amino-2,4,6-tribromobenzylidene)-3,4-dichlorophenylphosphonamidate, O-(1-methyl-2-methoxycarbonylvinyl) N-(α-amino-2-methyl-4,5-dichlorobenzylidene)-2-methoxyphenylphosphonamidate, O-(1-methyl-2-methoxycarbonylvinyl) N-(α-aminoethylidene)methoxymethylthionophosphonamidate, O-(1-methyl-2-methoxycarbonylvinyl) N-(α-aminoethylidene)-γ-methoxypropylthionophosphonamidate, O-(1-methyl-2-methoxycarbonylvinyl) N-(α-aminoethylidene)-δ-methoxybutylthionophosphonamidate, O-(1-methyl-2-methoxycarbonylvinyl) N-(α-aminoethylidene)-β-propoxyethylthionophosphonamidate, O-(1-methyl-2-methoxycarbonylvinyl) N-(α-aminoethylidene)-δ-ethoxybutylthionophosphonamidate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 34

| Preparation of a Dust | |
|---|---|
| Product of Example 2 | 10 |
| Powdered talc | 90 |

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, PEN, demeton, carbophenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-o-cresol, dinitrocyclohexylphenol, DNB, DNP, binapacril, azobenzene and the like; organic carbamate compounds such as carbaryl, ortho 5353 and the like; organic sulfur compounds such as phenothiazine, phenoxathin, lauryl thiocyanate, [bis(2-thiocyanoethyl)ether], isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes.

In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the woolly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of the present invention was demonstrated by experiments carried out for the control of a variety of insects.

Housefly

Approximately 25 to 30 four-day-old Housefly adults are placed in spherical wire mesh cages. The cages are mounted at the center of a rotating turntable so that each cage rotates on its own axis. At least three cages are provided for each test unit. Individual rotating cages are sprayed with aerosol formulations of the test compound at the indicated concentrations. Houseflies are then immediately removed to observation cages, observed for 60-minute knockdown, supplied with sugar-water food source, transferred to a holding room and observed for mortality 24 hours after treatment. The results of this test are shown in Table I.

Table I

| Test Compound | Rate (ppm): | Percent Control | | | | | | | | | | |
|---|---|---|---|---|---|---|---|---|---|---|---|---|
| | | 1024 | 512 | 256 | 128 | 64 | 32 | 16 | 8 | 4 | 2 | 1 |
| Product of Example 2 | k | 100 | 100 | 100 | 95* | 50* | 15* | 5* | 5* | 0 | 0 | 0 |
| | m | 100 | 100 | 100 | 100* | 95* | 25* | 15* | 5* | 10 | 10 | 0 |
| Product of Example 4 | k | 100 | 100 | 80 | 30 | — | — | — | — | — | — | — |
| | m | 100 | 100 | 100 | 100 | — | — | — | — | — | — | — | k = 60-minute knockdown
m = 24-hour mortality
*Values are averages of two replicates.

Southern Armyworm

Foliar portions of potted Dwarf Horticultural bean plants in first true leaf growth stage are sprayed with test solution containing a compound of this invention, or the soil of the potted plants is drenched with an aqueous emulsion of the test compound. The pots are then placed in holding racks provided with a subterranean water source. As indicated in the following table, the foliar spray and soil drench are also applied consecutively as one test at 1024 ppm and 64 lbs per acre. Three test plants are used for each test unit. Five third-instar larvae of Southern Armyworm are caged on treated plants for 48 hours. After this time observations are made for insect mortality. The results of this procedure are set forth in Table II.

TABLE II

| Test Compound | Rate | Percent Control | | | | | | | | | | |
|---|---|---|---|---|---|---|---|---|---|---|---|---|
| | | 1024 + 64 | 1024 | 512 | 256 | 128 | 64 | 32 | 16 | 8 | 4 | 2 | 1 |
| Product of Example 2 | ppm | | 100 | 70 | 30 | 10* | 0 | 0 | 0 | 0 | 0 | 0 | 0 |
| | #/A | 100 | — | — | — | — | 80 | 70 | 50 | 40 | 30 | 30 | 30 |
| Product of Example 4 | ppm | — | 100 | 100 | 100 | 100 | — | — | — | — | — | — | — |
| | #/A | — | — | — | — | — | 90 | — | — | — | — | — | — |

*Value is average of two replicates.

Mexican Bean Beetle

Foliar portions of potted Dwarf Horticultural bean plants in first true leaf growth stage are sprayed with test solution containing a compound of this invention, or the soil of the potted plants is drenched with an aqueous emulsion of the test compound. The pots are then placed in holding racks provided with a subterranean water source. As indicated in the following table, the foliar spray and soil drench are also applied consecutively as one test at 1024 ppm and 64 lbs per acre. Three test plants are used for each test unit. Five third-instar larvae of Mexican Bean Beetle are caged on treated plants for 48 hours. After this time observations are made for insect mortality. The results of these experiments are summarized in Table III.

TABLE III

| Test Compound | Rate | 1024 + 64 | 1024 | 512 | 256 | 128 | 64 | 32 | 16 | 8 | 4 | 2 | 1 |
|---|---|---|---|---|---|---|---|---|---|---|---|---|---|
| Product of Example 2 | ppm | 100 | 90 | 100 | 90 | 85* | 50 | 40 | 10 | 10 | 0 | 0 | 0 |
|  | #/A |  | — | — | — | — | 100 | 100 | 100 | 90 | 90 | 70 | 0 |
| Product of Example 4 | ppm | — | 100 | 100 | 100 | 100 | — | — | — | — | — | — | — |
|  | #/A |  | — | — | — | — | 100 | — | — | — | — | — | — |

*Value is average of two replicates.

Boll Weevil

Two leaves of a cotton plant are sprayed with test solution containing a compound of this invention at the indicated rates and are allowed to air dry. Boll weevils are then placed on the surface of the leaves, and the infested leaves are kept in a petri dish and are held for a period of 48 hours. After this time mortality is observed and compared to untreated controls.

In the soill drench applications 14-day-old cotton plants are watered with 30 ml of a solution of the test compound at the indicated rates. After 48 hours the primary leaves are removed and each is placed in a container with 10 adult Cotton Boll Weevils. Forty-eight hours after infestation mortality is observed and compared to untreated controls.

One test combines the procedures. The leaves are sprayed with the test compound at 1024 ppm and the soil drenched at 64 lbs per acre. Thereafter the primary leaves are removed and infested as above. Mortality observations are made 48 hours after infestation in comparison to controls.

The results of these tests are shown in Table IV.

TABLE IV

| Test Compound | Rate | 1024 + 64 | 1024 | 512 | 256 | 128 | 64 | 32 | 16 | 8 | 4 |
|---|---|---|---|---|---|---|---|---|---|---|---|
| Product of Example 2 | ppm | 100 | 100 | 100 | 70 | 70* | — | 0 | — | 0 | — |
|  | #/A |  | — | — | — | — | 80 | — | 10 | — | 0 |
| Product of Example 4 | ppm | — | 60 | 50 | 40 | 20 | — | — | — | — | — |
|  | #/A |  | — | — | — | — | 30 | — | — | — | — |

*Value is average of two replicates.

Two-Spotted Spider Mite

Potted horticultural beans at growth stage when primary leaves are approximately one inch long are infested with two-spotted spider mites 24 hours prior to treatment, ensuring establishment of adults and egg deposition at time of treatment.

The candidate compound is dissolved in a suitable solvent (acetone, methanol or other) or prepared as a wettable powder and diluted to appropriate concentrations with deionized water containing wetting and/or dispersing agents as appropriate.

Infested host plants, as above, are sprayed with test solution containing a compound of this invention, or the soil of the potted plants is drenched with an aqueous emulsion of the test compound. The pots are then placed in holding racks provided with a subterranean water source. As indicated in the following table, the foliar spray and soil drench are also applied consecutively as one test at 1024 ppm and 64 lbs per acre. Mortality is determined 48 hours after treatment by removing and observing one leaf from each plant. The results of these tests are set forth in Table V.

TABLE V

| Test Compound | Rate | 1024 + 64 | 1024 | 512 | 256 | 128 | 64 | 32 | 16 | 8 | 4 | 2 | 1 |
|---|---|---|---|---|---|---|---|---|---|---|---|---|---|
| Product of Example 2 | ppm | 65 | 55 | 30 | 10 | 10* | 0 | 0 | 0 | 0 | 0 | 0 | 0 |
|  | #/A |  | — | — | — | — | 60 | 55 | 50 | 30 | 25 | 20 | 10 |
| Product of Example 4 | ppm | — | 50 | 10 | 0 | 0 | — | — | — | — | — | — | — |
|  | #/A |  | — | — | — | — | 100 | — | — | — | — | — | — |

*Value is average of two replicates.

Cabbage Looper

Ten- to fourteen-day-old Henderson bush lima bean plants are planted in 3½ inches plastic pots using potting soil capped with ¼ inch of sand. The bean plants are then placed on a turntable and are sprayed with 100 ml of an aqueous solution or dispersion of a compound of this invention at the indicated concentrations, or the soil of the potted plants is drenched with 25 ml of an aqueous emulsion of the test compound. The plants are allowed to dry, and a leaf is removed from each and placed in a petri dish on top of a piece of wetted filter paper. Ten third-instar larvae of the Cabbage Looper are then placed on the leaf, and the petri dish is covered. Observations of mortality are made after 48 hours and are compared to untreated controls. Results of these tests are shown in Table VI.

TABLE VI

| Test Compound | Rate | \multicolumn{11}{c}{Percent Control} |
|---|---|---|---|---|---|---|---|---|---|---|---|---|
| | | 1024 | 512 | 256 | 128 | 64 | 32 | 16 | 8 | 4 | 2 | 1 |
| Product of Example 2 | ppm | — | — | — | 50 | 40 | 20 | 20 | 0 | 0 | 0 | 0 |
| | #/A | — | — | — | — | 80 | 70 | 50 | 40 | 30 | 30 | 30 |
| Product of Example 4 | ppm | 40 | 20 | 20 | 20 | — | — | — | — | — | — | — |
| | #/A | — | — | — | — | 90 | — | — | — | — | — | — |

Yellow Fever Mosquito Larvae

Aliquots of 100 ml of tap water containing various concentrations of the product of Example 2 are each supplied with 20 1-day-old Yellow Fever Mosquito larvae (*aedes aegypti* L.). The larvae are maintained at 25° C and are fed with malt yeast powder. After 13 days, when the pupae of untreated insects have hatched, the mortality percentages are calculated in comparison with the untreated controls. The results are indicated in Table VII.

TABLE VII

| Test Compound | Rate (ppm) | \multicolumn{5}{c}{Percent Control} |
|---|---|---|---|---|---|---|
| | | 10 | 1.0 | 0.1 | 0.01 | 0.001 |
| Product of Example 2 | | 100* | 100* | 90* | 65* | 70 |

*Values are averages of two replicates.

Pea Aphid

Windsor Broad Bean plants grown under greenhouse conditions, in the first true leaf growth stage and in soil of low moisture content are sprayed with test solution containing a compound of this invention, or the soil of the potted plants is drenched with 25 ml of an aqueous emulsion of the test compound. The pots are then placed in holding racks provided with a subterranean water source. Adult pea aphids are transferred to the foliar portion of the treated plants and held there for a period of 48 hours. After this time insect mortality is determined by observation in comparison to controls. The results of these procedures are shown in Table VIII.

Southern Corn Rootworm

Two germinating corn seeds and two ml of test compound formulated at the indicated concentrations are placed in plastic cups equipped with perforated cardboard covers. After 30 minutes 5 grams of soil mix (loam:sand, 2:1) are added to the cup and the contents are mixed. Five Southern Corn Rootworm larvae are then placed on the surface of the soil. The cups are then covered and held for 72-hour mortality observations. The results of this procedure can be seen in Table IX.

TABLE IX

| Test Compound | Rate (lbs/A) | \multicolumn{7}{c}{Percent Control} |
|---|---|---|---|---|---|---|---|---|
| | | 64 | 32 | 16 | 8 | 4 | 2 | 1 |
| Product of Example 2 | | 100 | 100 | 100 | 100 | 100 | 100 | 20 |

Green Peach Aphid

Dwarf Nasturtiums are planted in 3½ inches plastic pots containing potting soil capped with ¼ inch of sand. Ten- to fourteen-day-old plants are placed on a revolving table in a mist chamber and sprayed with 100 ml of a solution containing a compound of this invention at the indicated concentrations. After the leaves have dried, an untreated leaf infested with 10 to 20 Green Peach Aphids is placed on a treated leaf. As the untreated leaf wilts, the aphids crawl onto the treated leaf. Mortality is recorded in comparison to untreated controls 48 hours after infestation of the treated plant.

In the soil drench method similar plants are placed in a holding room, and water is withheld for 24 hours. After this time 25 ml of an aqueous emulsion containing a compound of this invention at the concentrations indicated are pipetted onto the sand caps. An infested leaf, as above, is placed on the treated plants 24 hours after the soil drench is applied. Mortality is recorded 48 hours after infestation.

The results of these tests are set forth in Table X.

TABLE VIII

| Test Compound | Rate | \multicolumn{11}{c}{Percent Control} |
|---|---|---|---|---|---|---|---|---|---|---|---|---|
| | | 1024 | 512 | 256 | 128 | 64 | 32 | 16 | 8 | 4 | 2 | 1 |
| Product of Example 2 | ppm | — | — | — | 100 | 100 | 100 | 100 | 40 | 10 | 0 | 0 |
| Product of Example 4 | ppm | 100 | 100 | 100 | 90 | — | — | — | — | — | — | — |
| | #/A | — | — | — | — | 100 | — | — | — | — | — | — |

TABLE X

| Test Compound | Rate | \multicolumn{11}{c}{Percent Control} |
|---|---|---|---|---|---|---|---|---|---|---|---|---|
| | | 1024 | 512 | 256 | 128 | 64 | 32 | 16 | 8 | 4 | 2 | 1 |
| Product of Example 2 | ppm | — | — | — | 90 | 80 | 0 | 0 | 0 | 0 | 0 | 0 |
| | #/A | — | — | — | — | 100 | 100 | 100 | 100 | 100 | 100 | 0 |
| Product of Example 4 | ppm | 100 | 100 | 90 | 100 | — | — | — | — | — | — | — |
| | #/A | — | — | — | — | 100 | — | — | — | — | — | — |

Black Bean Aphid

Snap beans are planted in 3½ inches plastic pots containing potting soil capped with ¼ inch of sand. Ten- to fourteen-day-old plants are placed on a revolving table in a mist chamber and sprayed with 100 ml of a solution containing a compound of this invention at the indicated concentrations. After the leaves have dried, an untreated leaf infested with 10 to 20 Black Bean Aphids is placed on a treated leaf. As the untreated leaf wilts, the aphids crawl onto the treated leaf. Mortality is recorded in comparison to untreated controls 48 hours after infestation of the treated plant.

In the soil drench method similar plants are placed in a holding room, and water is withheld for 24 hours. After this time 25 ml of an aqueous emulsion containing a compound of this invention at the concentrations indicated are pipetted onto the sand caps. An infested leaf, as above, is placed on the treated plants 24 hours after the soil drench is applied. Mortality is recorded 48 hours after infestation.

These two procedures are combined for simultaneous testing at 1024 ppm and 64 lbs per acre. The results of all of these tests are shown in Table XI.

TABLE XI

| Test Compound | Rate ppm #/A | Percent Control | | | | |
|---|---|---|---|---|---|---|
| | | 1024 + 64 | 1024 | 512 | 256 | 128 |
| Product of Example 2 | | 100 | 100 | 100 | 100 | 100 |

German Cockroach

Ten adult German cockroaches are first anesthetized with carbon dioxide and thereafter dipped into a 100 ml solution of the test compound at the indicated concentration. Thereafer the cockroaches are placed in holding cups and supplied with water as required. Mortality of the roaches is observed 48 hours after treatment in comparsion to untreated controls. The results of this testing are set forth in Table XII.

TABLE XII

| Test Compound | Rate (ppm) | Percent Control | | | | | |
|---|---|---|---|---|---|---|---|
| | | 1024 | 512 | 256 | 128 | 64 | 32 |
| Product of Example 2 | | 100 | 100 | 80 | 20 | 10 | 0 |

I claim:

1. A compound of the formula $$R^6-(X^1)_m-\underset{\underset{\underset{R^5-C-N}{\overset{\|}{N}}}{|}}{\overset{\overset{X^2}{\|}}{P}}-O-\underset{\underset{R^4}{\underset{|}{R^3}}}{\overset{\overset{R^1}{|}}{C}}=C-\overset{\overset{O}{\|}}{C}-O-R^2$$

wherein $X^1$ and $X^2$ are independently selected from the group consisting of oxygen and sulfur; $m$ is the integer 0 or 1; $R^1$ is selected from the group consisting of hydrogen and lower alkyl; $R^2$ is lower alkyl; $R^3$ and $R^4$ are independently selected from the group consisting of hydrogen and lower alkyl; $R^5$ is selected from the group consisting of hydrogen, lower alkyl, lower alkoxy, lower alkylthio, amino and wherein Y is selected from the group consisting of lower alkyl, halogen, lower alkoxy, lower alkylthio, nitro and cyano; and $n$ is an integer from 0 to 3; and $R^6$ is selected from the group consisting of lower alkyl, lower alkenyl, lower alkoxyalkyl and wherein Z is selected from the group consisting of lower-alkyl, halogen, lower alkoxy, lower alkylthio, nitro and cyano; and $p$ is an integer from 0 to 3.

2. A method of controlling insects which comprises contacting said insects with an insecticidal composition comprising an inert carrier and, as an essential active ingredient, in a quantity toxic to insects, a compound of claim 1.

3. The compound of claim 1, 0-(1-methyl-2-methoxycarbonylvinyl) N-(α-aminoethylidene)ethylthionophosphonamidate.

4. The compound of claim 1, 0-(1-methyl-2-isopropoxycarbonylvinyl) N-(α-aminoethylidene)ethylthionophosphonamidate.

5. The compound of claim 1, 0-(1-methyl-2-isopropoxycarbonylvinyl) N-(α-aminobenzylidene)ethylthionophosphonamidate.

6. The compound of claim 1, 0-(1-methyl-2-methoxycarbonylvinyl) N-(α-amino-α-methoxymethylidene)ethylthionophosphonamidate.

7. The compound of claim 1, 0-(1-methyl-2-isopropoxycarbonylvinyl) N-(aminomethylidene)ethylthionophosphonamidate.

8. The compound of claim 1, 0-(1-methyl-2-isopropoxycarbonylvinyl) N-(α-amino-α-methylthiomethylidene)ethylthionophosphonamidate.

9. The compound of claim 1, 0-(1-ethyl-2-ethoxycarbonylvinyl) 0-ethyl N-(α-amino-2-methylbenzylidene)phosphoramidate.

10. An insecticidal composition comprising an inert carrier and, as an essential active ingredient, in a quantity toxic to insects, a compound of claim 1.

* * * * *